(12) United States Patent
Hanafusa et al.

(10) Patent No.: US 10,488,374 B2
(45) Date of Patent: Nov. 26, 2019

(54) PREPROCESSING DEVICE AND ANALYSIS SYSTEM PROVIDED WITH SAME

(71) Applicant: SHIMADZU CORPORATION, Kyoto-shi, Kyoto (JP)

(72) Inventors: Nobuhiro Hanafusa, Kyoto (JP); Shin Nakamura, Kyoto (JP); Hiroshi Tanihata, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 302 days.

(21) Appl. No.: 15/507,395

(22) PCT Filed: Sep. 2, 2014

(86) PCT No.: PCT/JP2014/073056
§ 371 (c)(1),
(2) Date: Feb. 28, 2017

(87) PCT Pub. No.: WO2016/035139
PCT Pub. Date: Mar. 10, 2016

(65) Prior Publication Data
US 2017/0284982 A1 Oct. 5, 2017

(51) Int. Cl.
*G01N 1/10* (2006.01)
*G01N 27/62* (2006.01)
(Continued)

(52) U.S. Cl.
CPC ............... *G01N 30/24* (2013.01); *G01N 1/10* (2013.01); *G01N 27/62* (2013.01); *G01N 30/06* (2013.01);
(Continued)

(58) Field of Classification Search
CPC ........ G01N 30/06; G01N 30/24; G01N 30/36; G01N 30/88; G01N 30/466; G01N 1/10;
(Continued)

(56) References Cited

U.S. PATENT DOCUMENTS

2005/0191760 A1 9/2005 Heath et al.
2011/0157580 A1 6/2011 Nogami et al.
(Continued)

FOREIGN PATENT DOCUMENTS

| EP | 1029228 A1 | 8/2000 |
| EP | 2543994 A1 | 1/2013 |
| JP | 2010-60474 A | 3/2010 |

OTHER PUBLICATIONS

Schug, K., and Fan, H., "Hyphenation of flow-injection analysis with mass spectrometry: a versatile and high-throughput technique", Current trends in mass spectrometry, vol. 10, No. 2, p. 26-33 (2012).*
(Continued)

*Primary Examiner* — Benjamin L Lebron
(74) *Attorney, Agent, or Firm* — Sughrue Mion, PLLC

(57) ABSTRACT

The present invention provides a preprocessing device of a more compact structure, and an analysis system provided with the same. A preprocessing device (1) includes a container holding section (12), a filtration port (30), and a transport arm (24). The container holding section (12) holds a separation container (50) and a collection container (54). The filtration port (30) separates a sample by applying pressure to a sample in the separation container (50). The transport arm (24) transports the separation container (50) and the collection container (54) held by the container holding section (12) from a predetermined transport position. The container holding section (12) holds the separation container (50) and the collection container (54) in an annular or arch-shaped holding region formed on an outer circumference of the filtration port (30), and sequentially moves the separation container (50) and the collection container (54) to the transport position by shifting the separation container (Continued)

(50) and the collection container (54) in the circumferential direction of the holding region.

11 Claims, 20 Drawing Sheets

(51) Int. Cl.
| | |
|---|---|
| *G01N 30/06* | (2006.01) |
| *G01N 30/24* | (2006.01) |
| *G01N 30/36* | (2006.01) |
| *G01N 30/88* | (2006.01) |
| *G01N 35/02* | (2006.01) |
| *G01N 30/00* | (2006.01) |
| *G01N 35/00* | (2006.01) |
| *G01N 35/04* | (2006.01) |
| *G01N 35/10* | (2006.01) |
| *G01N 1/40* | (2006.01) |

(52) U.S. Cl.
CPC ............ *G01N 30/36* (2013.01); *G01N 30/88* (2013.01); *G01N 35/025* (2013.01); *G01N 35/04* (2013.01); *G01N 1/405* (2013.01); *G01N 2030/009* (2013.01); *G01N 2030/8804* (2013.01); *G01N 2035/00485* (2013.01); *G01N 2035/0441* (2013.01); *G01N 2035/1053* (2013.01)

(58) Field of Classification Search
CPC .. G01N 1/4055; G01N 1/405; G01N 35/0092; G01N 35/02; G01N 35/04; G01N 35/1095; G01N 35/025; G01N 2035/0441; G01N 2035/0443; G01N 2035/0455; G01N 2035/0544; G01N 2035/1058; G01N 2035/0485; G01N 2001/4061; G01N 2030/009; G01N 2030/8804; G01N 27/62; G01N 2035/00485; G01N 2035/0448; G01N 2035/1053; H01J 49/00

See application file for complete search history.

(56) References Cited

U.S. PATENT DOCUMENTS

| | | | | |
|---|---|---|---|---|
| 2012/0079875 | A1* | 4/2012 | Nogami | G01N 1/4055 73/61.59 |
| 2014/0057255 | A1* | 2/2014 | Holmes | C12Q 1/6883 435/6.11 |

OTHER PUBLICATIONS

International Search Report of PCT/JP2014/073056, dated Dec. 9, 2014 (PCT/ISA/210).

Communication dated Apr. 17, 2018, from the European Patent Office in counterpart European Application No. 14901289.0.

* cited by examiner

PREPROCESSING DEVICE AND ANALYSIS SYSTEM PROVIDED WITH SAME

CROSS REFERENCE TO RELATED APPLICATIONS

This application is a U.S. National Stage of Application No. PCT/JP2014/073056, filed Sep. 2, 2014. the contents of all of which are incorporated herein by reference.

TECHNICAL FIELD

The present invention relates to a preprocessing device for collecting a sample extracted by a separation container into a collection container and for preprocessing the sample, and an analysis system provided with the same.

BACKGROUND ART

For example, at the time of analyzing a component contained in a sample of biological origin, such as whole blood, blood serum, a dried blood spot or urine, analysis is sometimes performed after preprocessing the sample by a preprocessing device. For example, the preprocessing is a process of removing a specific component in the sample, which is not necessary for analysis, and extracting a necessary component, or a process of condensing or drying an extracted sample. Various structures are conventionally proposed as a preprocessing device for automatically performing such preprocessing (for example, see Patent Document 1).

For example, Patent Document 1 discloses a structure according to which a plurality of cartridges (separation containers) is held and transported by a common transport mechanism, each cartridge containing a separating agent through which a specific component in a sample is separated. The plurality of cartridges is sequentially transported by the transport mechanism to a pressure application mechanism provided at a predetermined position, and samples are extracted by application of pressure by the pressure application mechanism. A plurality of receiving containers (collection containers) for receiving extracted liquid from the cartridges is transported, at below the cartridges, by a transport mechanism different from that of the cartridges, and extraction of samples is continuously performed.

PRIOR ART DOCUMENTS

Patent Documents

Patent Document 1: JP 2010-60474 A

SUMMARY OF THE INVENTION

Problems to be Solved by the Invention

With a conventional preprocessing device as disclosed in Patent Document 1, separation containers and collection containers cannot be transported by transport mechanisms while a sample extraction process is performed at the pressure application mechanism. Accordingly, an already extracted sample cannot be removed during the extraction process for another sample, and there is a limit to increasing the preprocessing efficiency.

Accordingly, it is conceivable to separately provide a filtration section for separating a specific component in a sample, and to transport the separation containers and the collection containers to the filtration section and to sequentially send out a collection container with extracted sample. However, if such a filtration section is separately provided, the size of the device is increased by the amount of the installation space.

The present invention has been made in view of the above circumstances, and its object is to provide a preprocessing device of a more compact structure, and an analysis system provided with the same. Furthermore, the present invention has its object to provide a preprocessing device which is capable of increasing preprocessing efficiency, and an analysis system provided with the same.

Means for Solving the Problems

A preprocessing device of the present invention includes a container holding section, a filtration section and a transport section. The container holding section holds a plurality of containers including a separation container with a separating layer through which a specific component in a sample is separated and a collection container for collecting a sample extracted by the separating layer. The filtration section separates a sample by the separating layer by applying pressure to a sample in the separation container. The transport section transports a container held by the container holding section from a predetermined transport position. The container holding section holds the plurality of containers in an annular or arch-shaped holding region formed on an outer circumference of the filtration section, and sequentially moves the plurality of containers to the transport position by shifting the plurality of containers in a circumferential direction of the holding region.

According to this configuration, a plurality of containers held in the holding region may be sequentially moved to the transport position and be transported from the transport position by shifting the containers in the circumferential direction. Such a holding region is formed to have an annular or arch shape, and a more compact structure may be achieved by securing an installation space for the filtration section in a vacant space at a center portion of the holding region.

Also, by providing the filtration section at the center portion of the annular or arch-shaped holding region, the distance between a plurality of containers held in the holding region and the filtration section may be made relatively small. Accordingly, the time required to transport each container to the filtration section may be reduced, and the preprocessing efficiency may be increased.

The separation container and the collection container may be installed in the container holding section in a state where the separation container and the collection container are piled up.

According to this configuration, separate holding regions do not have to be provided for the separation container and the collection container, and thus, a greater number of containers may be held in a small holding region. Accordingly, the holding region for the containers may be made small, and a more compact structure may be achieved.

The container holding section may include a rotating section that rotates on a horizontal plane, and a plurality of container racks that can be detachably mounted to the rotating section, each container rack being for holding a plurality of containers.

According to this configuration, a plurality of containers may be held by each of a plurality of container racks which can be detachably mounted to the rotating section. By dividing and holding the containers by a plurality of container racks, each container rack is allowed to be individually mounted to or dismounted from the rotating section. Accordingly, even while processing is performed on a container which is held by one of the container racks, other container racks may be mounted or dismounted and other tasks may be performed, and thus, the preprocessing efficiency may be increased.

The preprocessing device may further include a detection section configured to detect that a container held by the container holding section is protruded above a predetermined position.

According to this configuration, in a case where a container which is held by the container holding section is protruded above the predetermined position due to installation error or the like, such a situation may be detected. Accordingly, an abnormality may be effectively prevented from occurring at the time of transporting the container by the transport section, and thus, the preprocessing efficiency may be increased.

Particularly, in a case where the separation container and the collection container are installed in the container holding section in a state where they are piled up, the position of the separation container and the collection container, which are piled up, is easily shifted. Accordingly, by detecting the shift in the containers by the detection section in such a case, an abnormality may be more effectively prevented from occurring at the time of transporting the containers by the transport section.

The preprocessing device may further include a notification section configured to issue a notification about protrusion in a case where protrusion of a container above the predetermined position is detected by the detection section.

According to this configuration, an analyst who noticed the notification from the notification section may check the state of the containers which are held by the container holding section. Accordingly, preprocessing may be performed after the shift of the containers is surely corrected.

The preprocessing device may further include a pressing section configured to push a container held by the container holding section into the container holding section in a case where the container is protruded above a predetermined position.

According to this configuration, in a case where a container which is held by the container holding section is protruded above the predetermined position due to installation error or the like, the container may be pushed into the container holding section by the pressing section, and the preprocessing may be performed after the shift of the container is surely corrected.

A plurality of types of separation containers may be held by the container holding section. In this case, the processing device may further include a storage section configured to store, in association with each other, a type of the separation container and a position of the separation container held by the container holding section, and a selection receiving section configured to receive selection of a type of the separation container. The transport section may transport the separation container of a selected type from the container holding section according to correspondence stored in the storage section.

According to this configuration, a separation container which is suitable for an analysis item may be selected, and the separation container may be reliably transported from the container holding section. Accordingly, a wider variety of analysis items may be handled, and also, preprocessing that is most suitable for the selected analysis item may be performed.

An analysis system of the present invention includes the preprocessing device, a liquid chromatograph into which a sample extracted by the preprocessing device is to be introduced, and a control section configured to automatically control the preprocessing device and the liquid chromatograph in coordination with each other.

Also, an analysis system of the present invention includes the preprocessing device, a mass spectrometry device into which a sample extracted by the preprocessing device is to be introduced, and a control section configured to automatically control the preprocessing device and the mass spectrometry device in coordination with each other.

Effects of the Invention

According to the present invention, the holding region is formed into an annular or arch shape, and an installation space for the filtration section is secured in a vacant space at the center portion of the holding region, and thus, a more compact structure may be achieved. Also, according to the present invention, the distance between a plurality of containers held in the holding region and the filtration section may be made relatively small, and thus, the time required to transport each container to the filtration section may be reduced, and the preprocessing efficiency may be increased.

MODE FOR CARRYING OUT THE INVENTION

Figure 1:
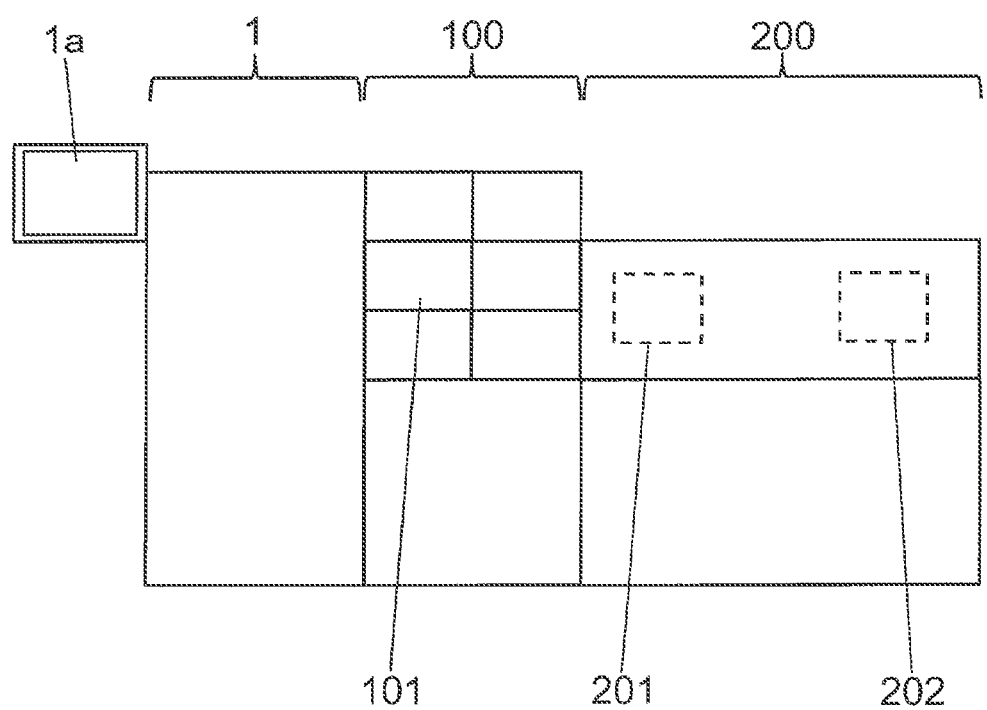
FIG. 1 is a schematic front view showing an example structure of an analysis system according to an embodiment of the present invention.

FIG. 1 is a schematic front view showing an example structure of an analysis system according to an embodiment of the present invention. The analysis system includes a preprocessing device 1, a liquid chromatograph (LC) 100, and a mass spectrometry device (MS) 200, and a sample which is subjected to preprocessing by the preprocessing device 1 is sequentially introduced into the LC 100 and the MS 200 and is analyzed. That is, the analysis system according to the present embodiment is structured by connecting a liquid chromatograph mass spectrometry device (LC/MS) to the preprocessing device 1. However, such a structure is not restrictive, and one of the LC 100 and the MS 200 may be omitted so that a sample which is subjected to preprocessing by the preprocessing device 1 is introduced into only one of the LC 100 and the MS 200.

The preprocessing device 1 performs various types of preprocessing, such as sample dispensing, reagent dispensing, agitation, and filtration, on a sample of biological origin, such as whole blood, blood serum, a dried blood spot, or urine. A sample extracted by such preprocessing is introduced into the LC 100 through an autosampler 101 which is provided to the LC 100. The LC 100 is provided with a column (not shown), and sample components separated in the process of the sample passing through the column are sequentially introduced into the MS 200. The MS 200 includes an ionization section 201 for ionizing a sample introduced from the LC 100, and a mass spectrometry section 202 for analyzing an ionized sample.

The preprocessing device 1 is provided with an operation display section 1a including a touch panel, for example. An analyst is allowed to perform input regarding operation of the preprocessing device 1 by performing operation on a display screen of the operation display section 1a, and is also allowed to check information about operation of the preprocessing device 1 displayed on the display screen of the operation display section 1a. Additionally, the structure where the operation display section 1a of a touch panel type is provided is not restrictive, and a display section structured by a liquid crystal display, and an operation section structured by operation keys or the like may be separately provided.

Figure 2:
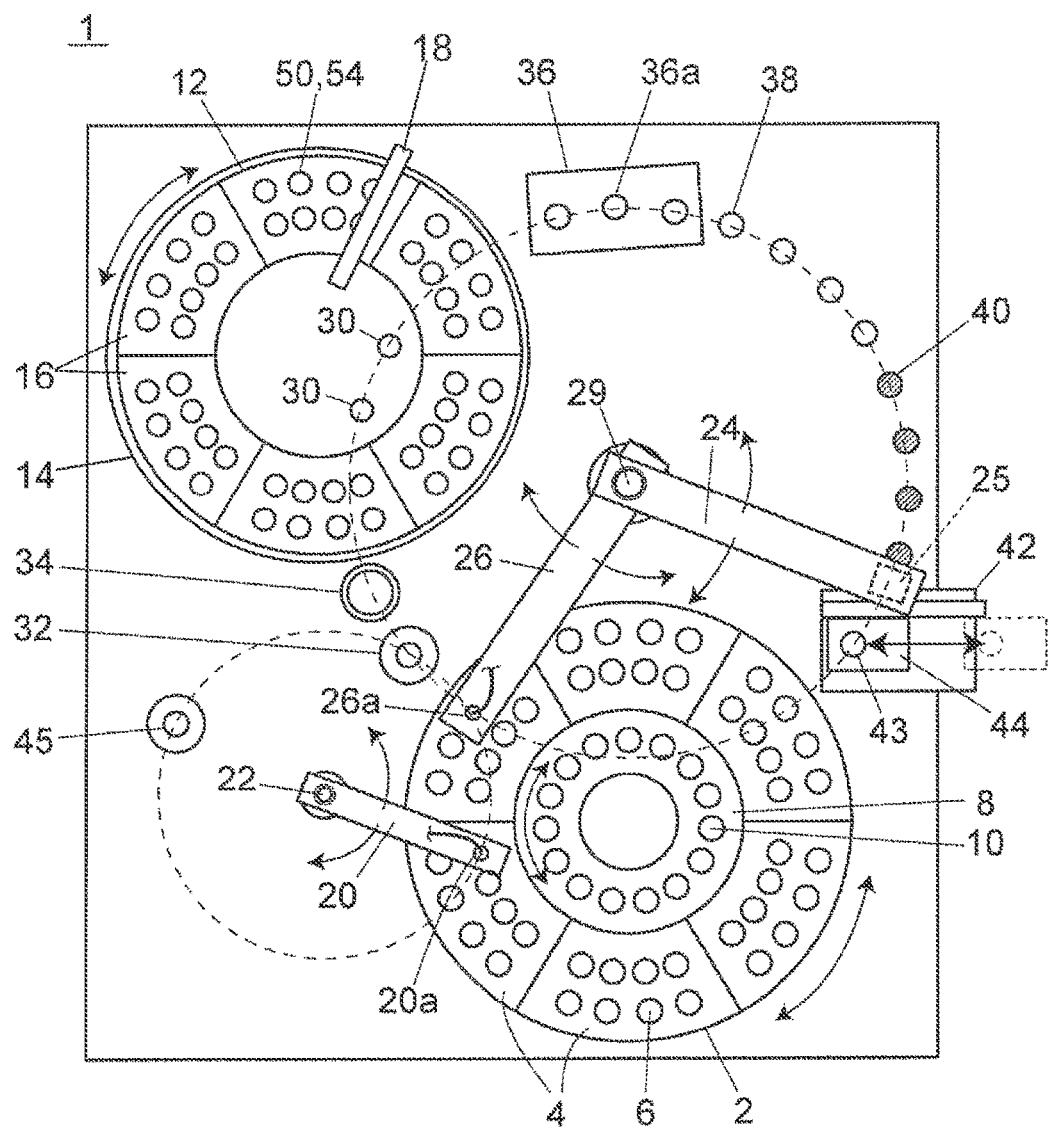
FIG. 2 is a plan view showing an example structure of a preprocessing device.

FIG. 2 is a plan view showing an example structure of the preprocessing device 1. The preprocessing device 1 uses one preprocessing kit, which is a set of a separation container 50 and a collection container 54, for each sample, and performs a preprocessing item (sample dispensing, reagent dispensing, agitation, filtration, etc.) set for each preprocessing kit. The preprocessing device 1 is provided with a plurality of processing ports for performing respective preprocessing items, and by installing a preprocessing kit containing a sample in one of the processing ports, the preprocessing item corresponding to the processing port is performed on the sample contained in the preprocessing kit.

As the processing ports, filtration ports 30, a dispensing port 32, a discard port 34, agitation ports 36a, temperature adjustment ports 38, 40, a transfer port 43, a washing port 45 and the like are provided in correspondence with the preprocessing items. These processing ports form a plurality of preprocessing sections for performing a plurality of preprocessing items. The preprocessing items here are types of preprocessing necessary to analyze analysis items specified by an analyst.

The separation container 50 and the collection container 54 forming the preprocessing kit is transported between the processing ports by a transport arm 24 as a transport section. A holding section 25 for holding the separation container 50 and the collection container 54 is formed on a tip end side of the transport arm 24. A base end portion side of the transport arm 24 is rotatably held around a vertical shaft 29. The transport arm 24 extends in a horizontal direction, and moves in such a way that the holding section 25 draws an arch on a horizontal plane when the transport arm 24 rotates around the vertical shaft 29. Each of the processing ports and other ports, which are transport destinations of the separation container 50 and the collection container 54, are all provided on the arch-shaped track which is drawn by the holding section 25.

A sample is dispensed into the preprocessing kit from a sample container 6. A plurality of sample containers 6 containing samples may be installed in a sample installation section 2, and samples are sequentially collected from the sample containers 6 by a sampling arm 20 as a sampling section. A plurality of sample racks 4 for holding a plurality of sample containers 6 are installed next to one another in a circle at the sample installation section 2. The sample installation section 2 rotates on the horizontal plane to move the sample racks 4 in a circumferential direction. The sample containers 6 may thus be sequentially moved to a predetermined sampling position. The sampling position here is on the track of a sampling nozzle 20a provided at a tip end portion of the sampling arm 20, and a sample is collected from the sample container 6 by the sampling nozzle 20a at the sampling position.

The sampling arm 20 is capable of rotating on the horizontal plane, around a vertical shaft 22 provided on a base end portion side, and of moving up and down in a vertical direction along the vertical shaft 22. The sampling nozzle 20a is held at the tip end portion of the sampling arm 20, facing downward in the vertical direction, and moves according to operation of the sampling arm 20 so as to draw an arch on the horizontal plane or to move up and down in the vertical direction.

The dispensing port 32 is provided on the track of the sampling nozzle 20a, at a position on the track of the holding section 25 of the transport arm 24. The dispensing port 32 is a port for dispensing a sample into an unused separation container 50 from the sampling nozzle 20a. An unused separation container 50 is transported to the dispensing port 32 by the transport arm 24.

A reagent installation section 8 for installing reagent containers 10 is provided at a center portion of the sample installation section 2 where the sample racks 4 are arranged next to one another in a circle. A reagent in the reagent container 10 installed in the reagent installation section 8 is collected by a reagent arm 26. The reagent arm 26 has its base end portion supported by the vertical shaft 29, which is common with that of the transport arm 24, and is capable of rotating on the horizontal plane around the vertical shaft 29, and of moving up and down in the vertical direction along the vertical shaft 29. A reagent addition nozzle 26a is held at a tip end portion of the reagent arm 26, facing downward in the vertical direction, and the reagent addition nozzle 26a moves according to operation of the reagent arm 26 so as to draw the same arch as the holding section 25 of the transport arm 24 on the horizontal plane or to move up and down in the vertical direction.

The reagent installation section 8 is capable of rotating on the horizontal plane independently of the sample installation section 2. A plurality of reagent containers 10 is arranged next to one another in a circle at the reagent installation section 8, and each reagent container 10 moves in the circumferential direction when the reagent installation section 8 is rotated. A desired reagent container 10 may thereby be moved to a predetermined reagent collection position. The reagent collection position is on the track of the reagent addition nozzle 26a provided at the tip end portion of the reagent arm 26, and a reagent is collected by the reagent addition nozzle 26a from the reagent container 10 at the reagent collection position. A reagent in the reagent container 10 is sucked into the reagent addition nozzle 26a, and is then dispensed into the separation container 50 installed at the dispensing port 32, and is thus added to the sample in the separation container 50.

The separation container 50 and the collection container 54 are held by a container holding section 12 provided at a different position from the sample installation section 2 and the reagent installation section 8. A plurality of preprocessing kits, each of which is a set of unused separation container 50 and collection container 54 that are piled up, are arranged next to one another in a circle at the container holding section 12. The container holding section 12 is provided with a rotating section 14, which rotates on the horizontal plane, and a plurality of container racks 16 which is detachably mounted to the rotating section 14.

Each container rack 16 is capable of holding a plurality of preprocessing kits. The plurality of container racks 16 are arranged next to one another in a circle on the rotating section 14. An annular holding region for holding a plurality of preprocessing kits is formed by the plurality of container racks 16 arranged next to one another in a circle. The rotating section 14 rotates on the horizontal plane to thereby shift each container rack 16 in the circumferential direction of the holding region. A plurality of preprocessing kits may thereby be sequentially moved to a predetermined transport position. The transport position here is on the track of the holding section 25 provided at the tip end portion of the transport arm 24, and the separation container 50 or the collection container 54 is held by the holding section 25 at the transport position to be transported to a transport destination port.

By dividing and holding the preprocessing kits by a plurality of container racks 16 in this manner, each container rack 16 is allowed to be individually mounted to or dismounted from the rotating section 14. Accordingly, even while processing is performed on the separation container 50 or the collection container 54 which is held by one of the container racks 16, other container racks 16 may be mounted or dismounted and other tasks may be performed, and thus, the preprocessing efficiency may be increased.

Additionally, the separation container 50 and the collection container 54 do not necessarily have to be held by the container holding section 12 through the container rack 16, and may alternatively be held directly by the container holding section 12, for example. Also, the separation container 50 and the collection container 54 do not necessarily have to be held by the container holding section 12 in a state where they are piled up, and the separation container 50 and the collection container 54 may alternatively be held separately from each other. Moreover, the plurality of container racks 16 do not necessarily have to be arranged next to one another in a circle, and may alternatively be arranged next to one another in an arch, for example. In this case, a plurality of separation containers 50 and collection containers 54 are held in an arch-shaped holding region instead of an annular holding region.

An analyst may install, at the container holding section 12, a plurality of types (for example, two types) of separation containers 50 with separating layers of different separation performances. These separation containers 50 are used according to the sample analysis items, and a separation container 50 corresponding to the analysis item specified by the analyst is selected and transported from the container holding section 12. The analysis item here is the type of analysis which is to be sequentially performed using a sample which has been subjected to preprocessing by the preprocessing device 1, and is the type of analysis to be performed by the LC 100 or the MS 200, for example.

Figure 3A:
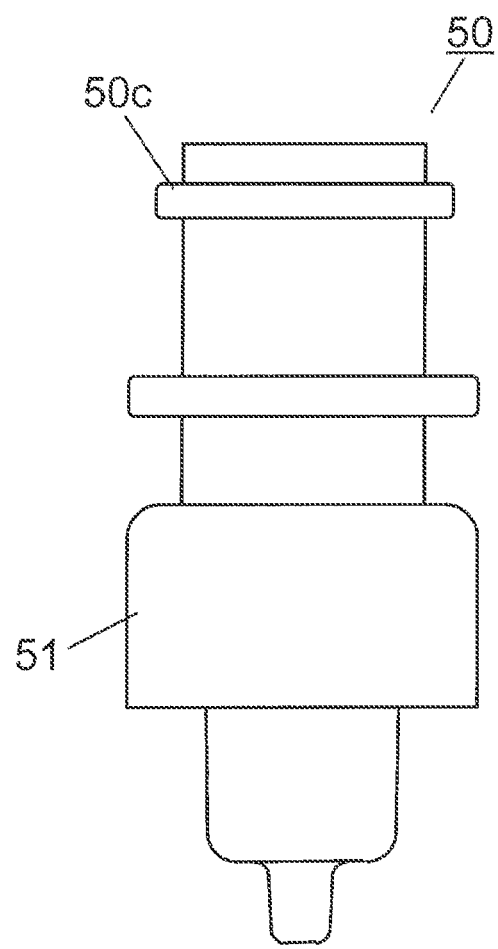
FIG. 3A is a side view showing an example structure of a separation container.
Figure 3B:
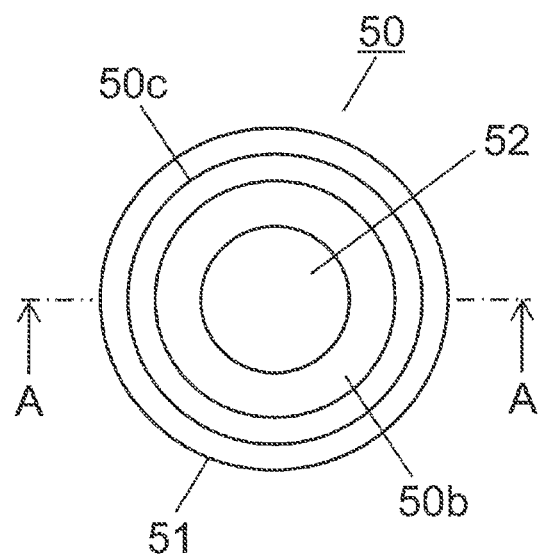
FIG. 3B is a plan view of the separation container shown in FIG. 3A.
Figure 3C:
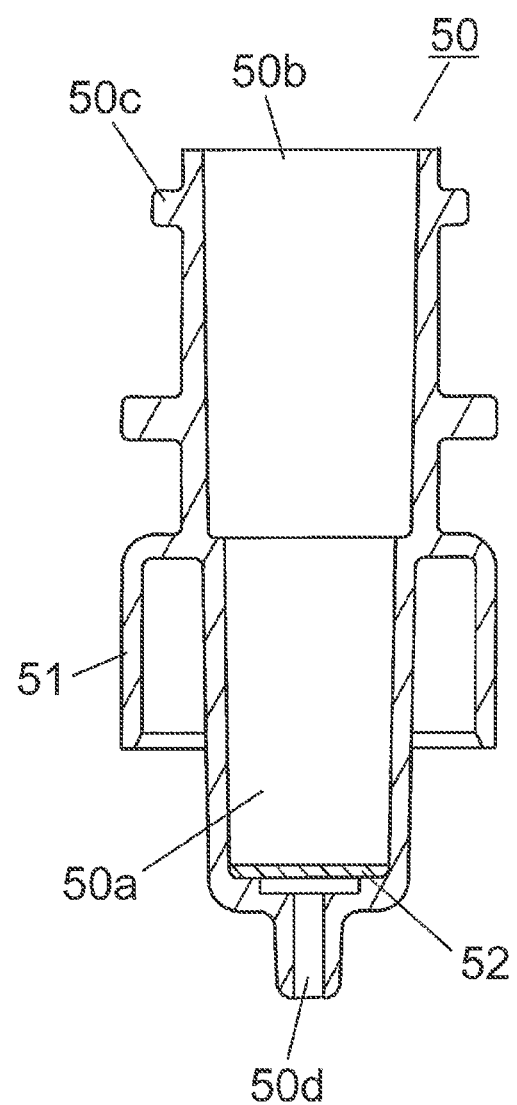
FIG. 3C is a cross-sectional view showing a cross-section taken along line A-A in FIG. 3B.
Figure 4A:
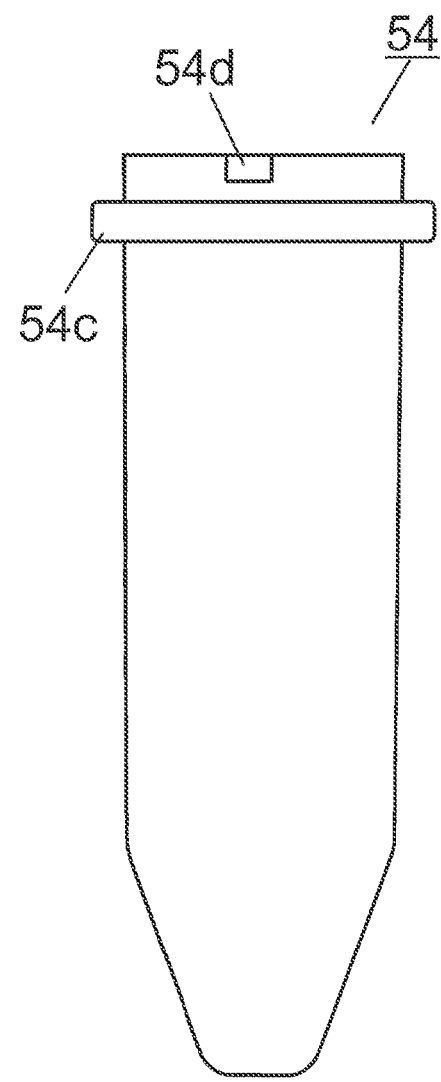
FIG. 4A is a side view showing an example structure of a collection container.
Figure 4B:
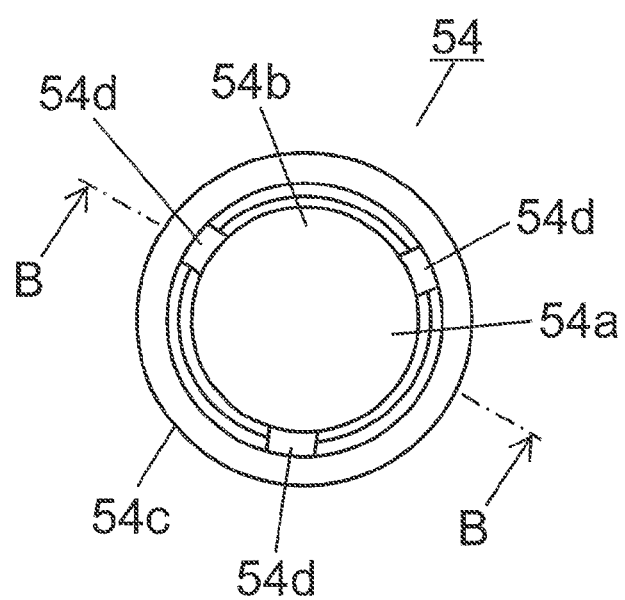
FIG. 4B is a plan view of the collection container in FIG. 4A.
Figure 4C:
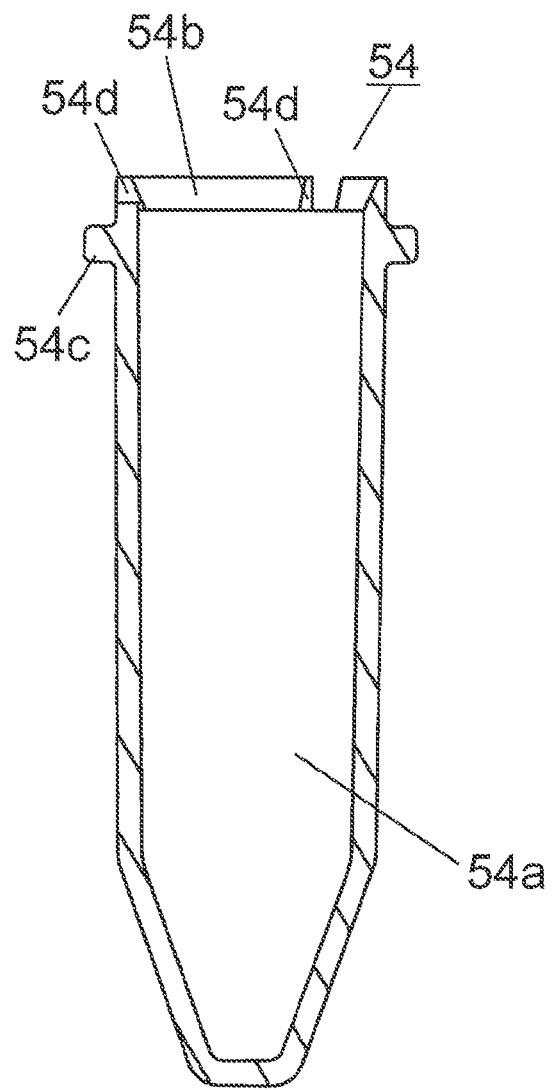
FIG. 4C is a cross-sectional view showing a cross-section taken along line B-B in FIG. 4B.
Figure 5:
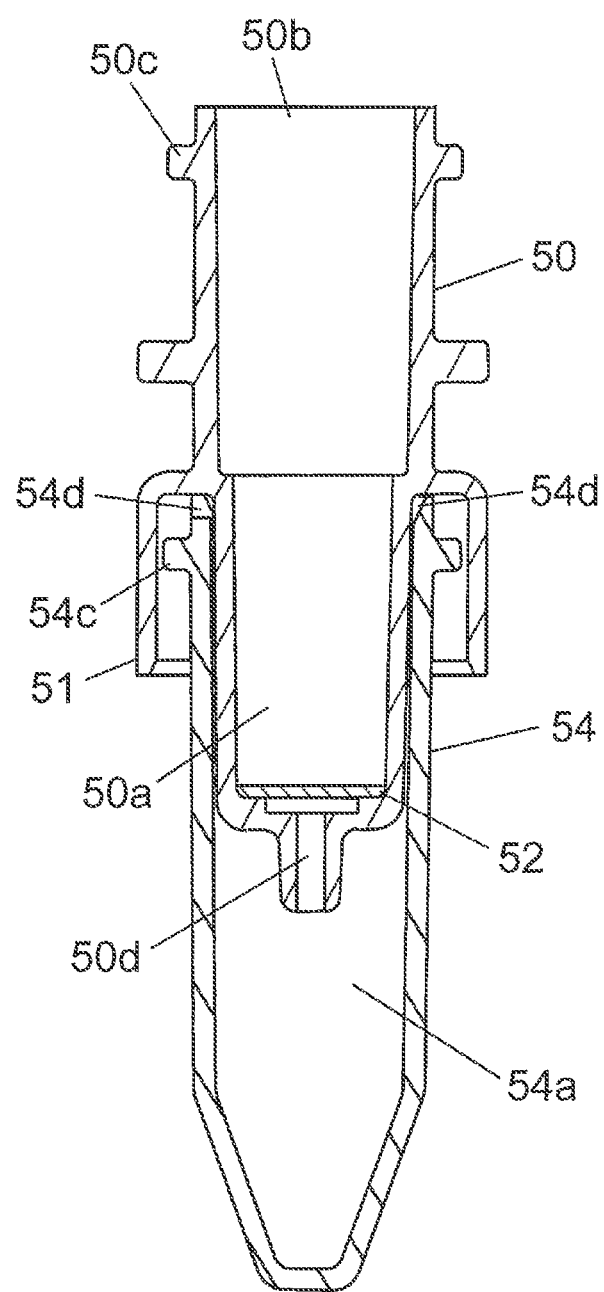
FIG. 5 is a cross-sectional view showing a preprocessing kit in a state where the separation container and the collection container are piled up.

FIG. 3A is a side view showing an example structure of the separation container 50. FIG. 3B is a plan view of the separation container 50 in FIG. 3A. FIG. 3C is a cross-sectional view showing a cross-section along A-A in FIG. 3B. FIG. 4A is a side view showing an example structure of the collection container 54. FIG. 4B is a plan view of the collection container 54 in FIG. 4A. FIG. 4C is a cross-sectional view showing a cross-section along B-B in FIG. 4B. FIG. 5 is a cross-sectional view showing a preprocessing kit in a state where the separation container 50 and the collection container 54 are piled up.

As shown in FIGS. 3A to 3C, the separation container 50 is a cylindrical container having an inner space 50a for containing a sample or a reagent. A separating layer 52 is provided at a bottom portion of the inner space 50a. The separating layer 52 is a separating agent or a separating film having a function of selectively separating a specific component in a sample by letting a sample pass through and by physically or chemically reacting with the specific component, for example.

As the separating agent forming the separating layer 52, ion exchange resin, silica gel, cellulose, or activated carbon may be used, for example. Also, as the separating film, a polytetrafluoroethylene (PTFE) film, a nylon film, a polypropylene film, a polyvinylidene difluoride film (PVDF) film, an acrylic copolymer film, a mixed cellulose film, a nitrocellulose film, a polyethersulfone film, an ion exchange film, or a glass fiber film may be used, for example.

As a deproteinization filter (separating film) for removing protein in a sample by filtration, a PTFE or acrylic copolymer film may be used, for example. In this case, to prevent clogging of the deproteinization filter, a pre-filter (not shown) may be provide on an upper side of the separating layer 52. As the pre-filter, a nylon film, a polypropylene film, or a glass fiber film may be used, for example. The pre-filter is for removing insoluble substances and foreign substances with relatively large particle diameters from a sample. The deproteinization filter may be prevented, by this pre-filter, from being clogged with insoluble substances and foreign substances with relatively large particle diameters.

An opening 50b for injecting a sample or a reagent is formed at an upper surface of the separation container 50. Also, an extraction opening 50d for extracting a sample which has passed through the separating layer 52 is formed at a lower surface of the separation container 50. A flange section 50c for engaging with the holding section 25 of the transport arm 24 is formed at an upper portion of an outer circumferential surface of the separation container 50, protruding in the circumferential direction.

A skirt section 51 which contacts the edge of the filtration port 30 when the separation container 50 is accommodated, together with the collection container 54, in the filtration port 30 is provided at a center portion of the outer circumferential surface of the separation container 50. The skirt section 51 is formed to have an L shape in cross-section, and protrudes in the circumferential direction from the outer circumferential surface of the separation container 50 and extends downward, and thereby forms a certain space to the outer circumferential surface of the separation container 50.

As shown in FIGS. 4A to 4C and FIG. 5, the collection container 54 is a cylindrical container for accommodating a lower portion of the separation container 50, and for collecting a sample extracted from the extraction opening 50d of the separation container 50. An opening 54b for inserting the lower portion of the separation container 50 is formed to an upper surface of the collection container 54. An inner space 54a for accommodating a part of the separation container 50 lower than the skirt section 51 is formed inside the collection container 54. As with the separation container 50, a flange section 54c for engaging with the holding section 25 of the transport arm 24 is formed at an upper portion of an outer circumferential surface of the collection container 54, protruding in the circumferential direction.

As shown in FIG. 5, in a state where the separation container 50 and the collection container 54 are piled up, the upper portion of the collection container 54 is placed inside the skirt section 51. The outer diameter of the separation container 50 is smaller than the inner diameter of the collection container 54. Accordingly, a small gap is formed between the outer circumferential surface of the separation container 50 accommodated in the inner space 54a of the collection container 54 and the inner circumferential surface of the collection container 54. The separation container 50 and the collection container 54 are installed in the container holding section 12 with the lower portion of the separation container 50 accommodated inside the collection container 54 (the state shown in FIG. 5).

Three cut-outs 54d are formed to the edge of the upper surface of the collection container 54. Accordingly, when the separation container 50 and the collection container 54 are piled up as shown in FIG. 5, the inside and the outside of the collection container 54 may be communicated through the cut-outs 54 even in a state where the upper surface of the collection container 54 is in contact with the inner surface of the skirt section 51. Additionally, the number of cut-outs 54d is not limited to three, and it may be two or less, or four or more. Also, a small hole may be formed instead of the cut-out 54d.

Referring back to FIG. 2, the filtration ports 30 are provided on the inside the container holding section 12. That is, an annular or arch-shaped holding region is formed by the plurality of container racks 16 arranged next to one another on the outer circumference of the filtration ports 30, and a plurality of separation containers 50 and collection containers 54 are held in the holding region. In this manner, because the holding region of the separation containers 50 and the collection containers 54 is formed into an annular or arch shape, and an installation space for the filtration ports 30 is secured in a vacant space at the center portion of the holding region, a more compact structure may be achieved.

Particularly, in the present embodiment, because the separation container 50 and the collection container 54 are held in the holding region in a state where they are piled up, separate holding regions do not have to be provided for the separation container 50 and the collection container 54. Therefore, a greater number of separation containers 50 and collection containers 54 may be held in a small holding region. Accordingly, the holding region for the separation containers 50 and the collection containers 54 may be made even smaller, and a more compact structure may be achieved.

Furthermore, by providing the filtration ports 30 at the center portion of the holding region which is formed into an annular or arch shape, the distances between the plurality of separation containers 50 and collection containers 54 held in the holding region and the filtration ports 30 may be made relatively small. Accordingly, the time required to transport the separation container 50 and the collection container 54 to the filtration port 30 may be reduced, and the preprocessing efficiency may be increased.

The filtration port 30 forms a filtration section for separating a sample by the separating layer 52 by applying pressure to a sample in the separation container 50. In the present embodiment, two filtration ports 30 are provided next to each other on the track of the holding section 25 of the transport arm 24, for example. The separation container 50 and the collection container 54 are installed in each filtration port 30 in a state where they are piled up as shown in FIG. 5, and a sample separated by the separating layer 52 in the separation container 50 by a negative pressure is collected by the collection container 54. Additionally, the separation container 50 and the collection container 54 do not necessarily have to be installed in the filtration port 30 in a state where they are piled up, and the separation container 50 and the collection container 54 may alternatively be installed separately. Also, the number of the filtration ports 30 is not limited to two, and it may be one or three or more.

Three agitation ports 36a are provided to an agitation section 36 provided near the container holding section 12, next to one another on the track of the holding section 25 of the transport arm 24, for example. The agitation section 36 has a mechanism for periodically and separately operating each of the agitation ports 36a on the horizontal plane. A sample in the separation container 50 disposed in each agitation port 36a may by agitated by such a mechanism. Additionally, the number of the agitation ports 36a is not limited to three, and it may be two or less, or four or more.

The temperature adjustment port 38, 40 is provided to a thermally conductive block temperature of which is controlled by a heater and a Peltier device, for example, and the temperature of the separation container 50 or the collection container 54 accommodated in the temperature adjustment port 38, 40 is adjusted to a certain temperature. The temperature adjustment port 38 is for the separation container 50, and four temperature adjustment ports 38 are arranged next to one another on the track of the holding section 25 of the transport arm 24, for example. The temperature adjustment port 40 is for the collection container 54, and like the temperature adjustment ports 38 for the separation containers 50, four temperature adjustment ports 40 are arranged next to one another on the track of the holding section 25 of the transport arm 24, for example. Additionally, the number of the temperature adjustment ports 38, 40 is not limited to four, and it may be three or less, or five or more.

Figure 6A:
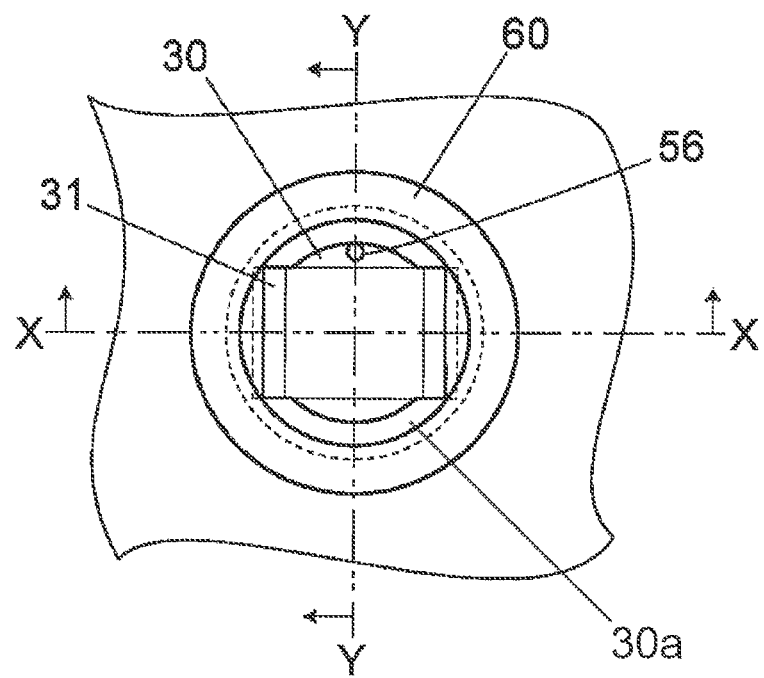
FIG. 6A is a plan view showing an example structure of a filtration port.
Figure 6B:
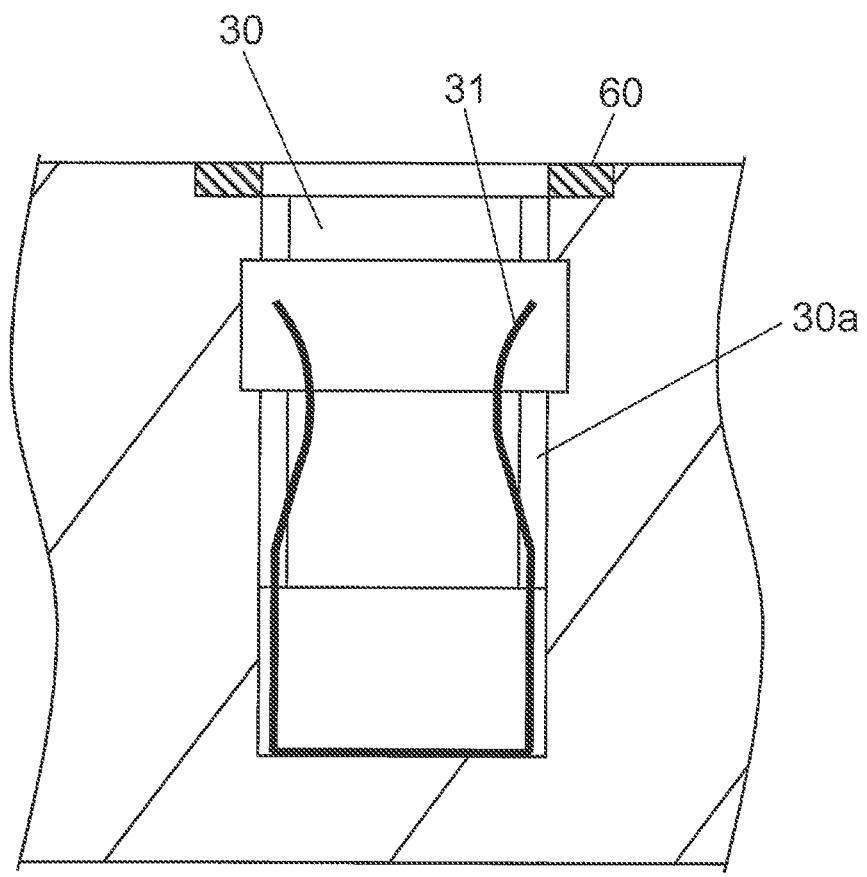
FIG. 6B is a cross-sectional view showing a cross-section taken along line X-X in FIG. 6A.
Figure 6C:
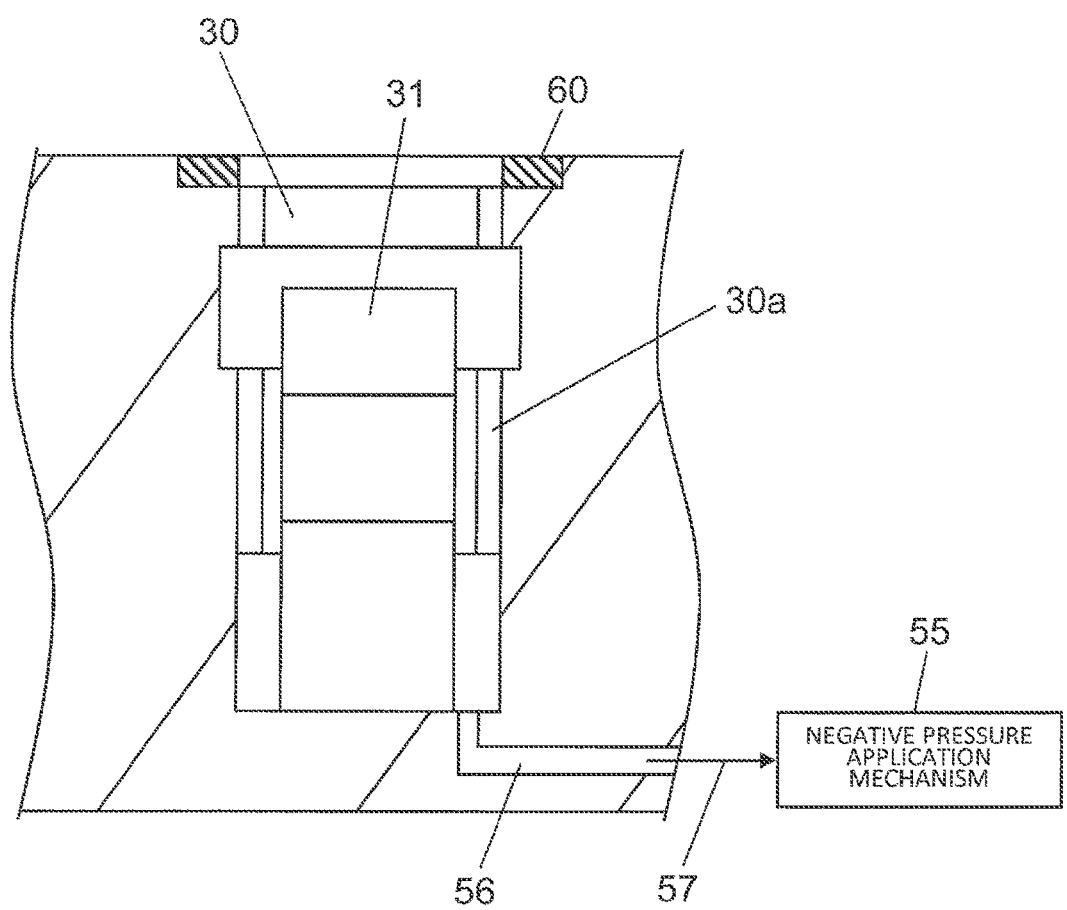
FIG. 6C is a cross-sectional view showing a cross-section taken along line Y-Y in FIG. 6A.
Figure 6D:
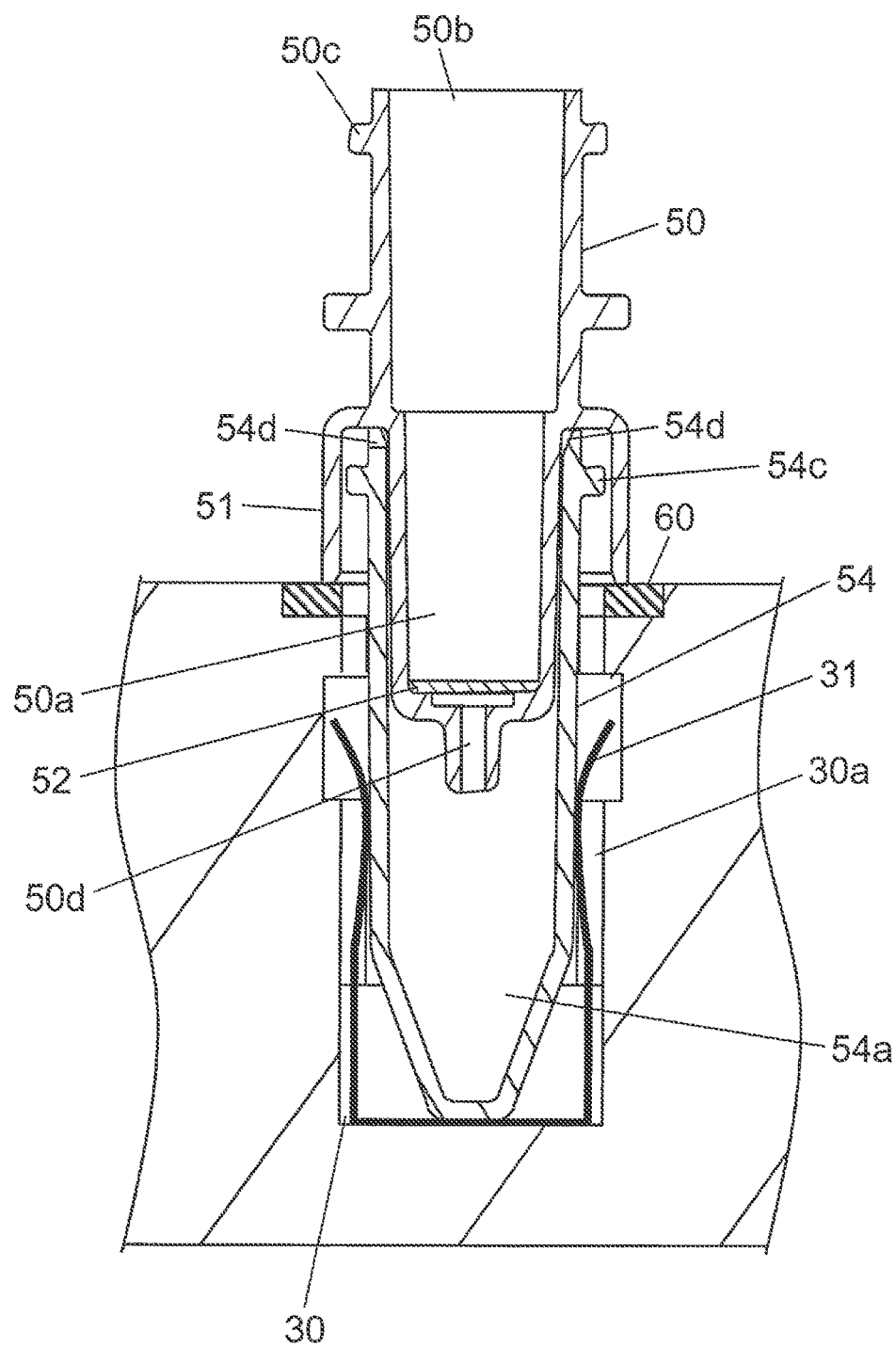
FIG. 6D is a cross-sectional view showing a state where the preprocessing kit is installed in the filtration port.

FIG. 6A is a plan view showing an example structure of the filtration port 30. FIG. 6B is a cross-sectional view showing a cross-section along X-X in FIG. 6A. FIG. 6C is a cross-sectional view showing a cross-section along Y-Y in FIG. 6A. FIG. 6D is a cross-sectional view showing a state where the preprocessing kit is installed in the filtration port 30.

The filtration port 30 is formed as a recessed section, for example, and the recessed section forms an installation space 30a for installing the preprocessing kit. That is, as shown in FIG. 6D, the separation container 50 and the collection container 54 transported by the transport arm 24 from the container holding section 12 are installed in the installation space 30a in a state where they are piled up. At this time, the collection container 54 is accommodated first in the installation space 30a, and then, the lower portion of the separation container 50 is accommodated in the inner space 54a of the collection container 54.

A holding member 31 for sandwiching and holding the collection container 54 is provided inside the filtration port 30. The holding member 31 is a U-shaped metal member which is open at the top, for example, and two arm sections extending upward form two leaf springs which are capable of elastically shifting in an inner diameter direction of the filtration port 30. The two leaf spring portions of the holding member 31 are curved or bent inward in such a way that the gap between the two is the smallest at a part between upper end portions and lower end portions, for example. The gap between the two leaf spring portions is greater than the outer diameter of the collection container 54 at the upper end portions and the lower end portions, and smaller than the outer diameter of the collection container 54 at the part where the gap is the smallest.

Due to the shape of the holding member 31 as described above, when the collection container 54 is inserted into the installation space 30a of the filtration port 30, the two leaf spring portions of the holding member 31 are opened as the collection container 54 is lowered, and the collection container 54 is held in the installation space 30a by the elastic force. The collection container 54 is equally pressed from two opposite directions by the two leaf spring portions of the holding member 31, and is held at a center portion of the installation space 30a. The holding member 31 is fixed inside the installation space 30a, and is prevented from being lifted together with the collection container 54 at the time of removal of the collection container 54.

A ring-shaped sealing member 60 having elasticity is provided at an edge of an opening section at an upper surface of the filtration port 30. The sealing member 60 is fitted in a pit provided at the edge of the opening section at the upper surface of the filtration port 30, for example. The material of the sealing member 60 is an elastic material such as silicone rubber or ethylene propylene rubber (EPDM), for example. When the collection container 54 and the separation container 50 are installed inside the installation space 30a of the filtration port 30, the lower end of the skirt section 51 of the separation container 50 comes into contact with the sealing member 60, and the installation space 30a is sealed by the skirt section 51. Additionally, the contact portion of the separation container 50 to the sealing member 60 is not limited to a member having the shape of the skirt section 51, and contact sections having various shapes, such as a flange section, are allowed, for example.

A channel 56 for reducing pressure communicates with the installation space 30a from a bottom surface of the filtration port 30. A channel 57 of a negative pressure application mechanism 55 is connected to the channel 56. The negative pressure application mechanism 55 includes a vacuum pump, for example, and forms a negative pressure application section which applies a negative pressure inside the installation space 30a. When the pressure inside the installation space 30a is reduced by the negative pressure application mechanism 55 in a state where the separation container 50 and the collection container 54 are accommodated in the filtration port 30, the pressure inside the installation space 30a becomes negative.

The inner space 54a of the collection container 54 communicates with the installation space 30a with negative pressure through the cut-outs 54d of the collection container 54 and the gap between the inner circumferential surface of the collection container 54 and the outer circumferential surface of the separation container 50. The upper surface of the separation container 50 is open to the atmosphere, and thus, a pressure difference is caused between the inner space 50a of the separation container 50 and the inner space 54a of the collection container 54 across the separating layer 52. Accordingly, only the component, of a sample contained in the inner space 50a of the separation container 50, which can pass through the separating layer 52 is separated by the separating layer 52 by the pressure difference, and is extracted into the inner space 54a side of the collection container 54.

Figure 7:
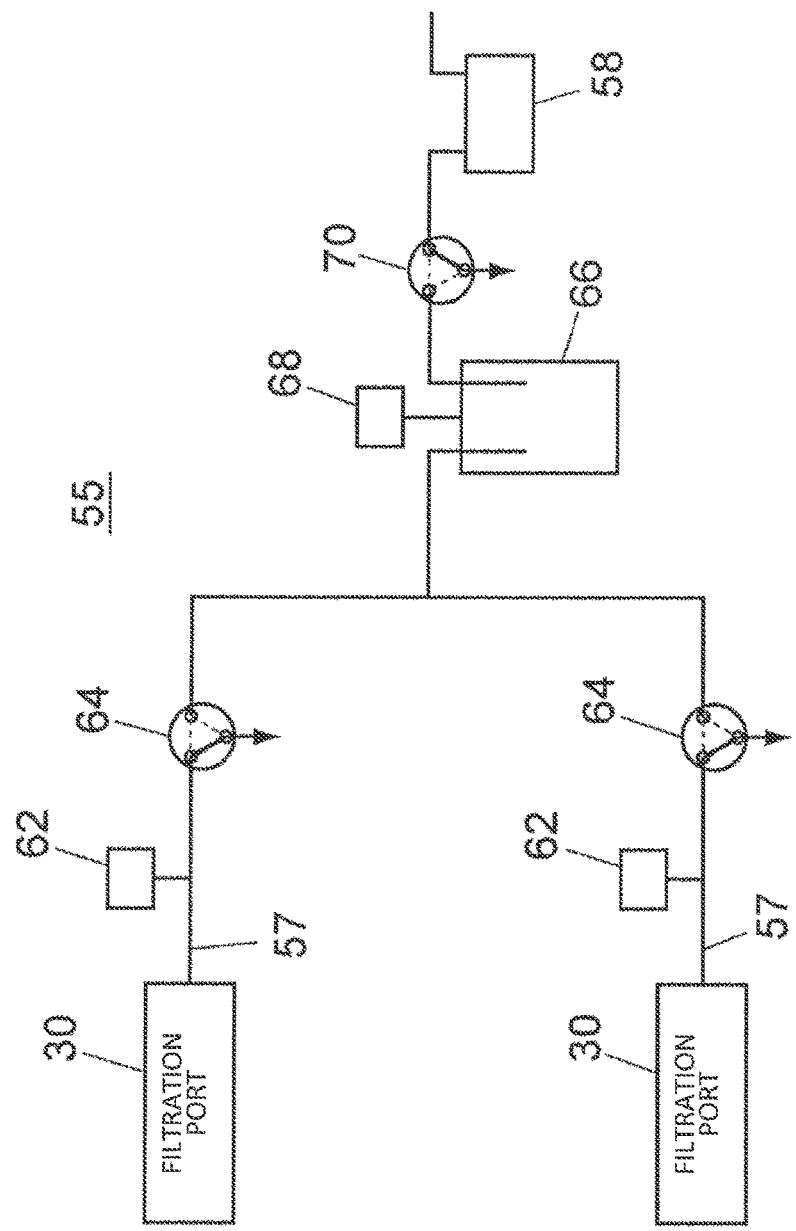
FIG. 7 is a schematic view showing an example structure of a negative pressure application mechanism.

FIG. 7 is a schematic view showing an example structure of the negative pressure application mechanism 55. Two filtration ports 30 are connected to a common vacuum tank 66. Each filtration port 30 and the vacuum tank 66 are connected by the channel 57, and a pressure sensor 62 and a three-way valve 64 are provided to each channel 57. The pressure inside the installation space 30a of each filtration port 30 is detected by the pressure sensor 62. Each three-way valve 64 is capable of switching to any one of a state where the filtration port 30 and the vacuum tank 66 are connected, a state where the channel 57 is open to the atmosphere on the side of the filtration port 30 (the state shown in FIG. 7), and a state where an end portion of the channel 57 on the side of the filtration port 30 is sealed.

A pressure sensor 68 is connected to the vacuum tank 66, and also, a vacuum pump 58 is connected to the vacuum tank 66 through a three-way valve 70. Accordingly, by switching the three-way valve 70, the vacuum pump 58 may be connected to the vacuum tank 66 as necessary to adjust the pressure inside the vacuum tank 66.

When performing a sample extraction process at one of the filtration ports 30, the filtration port 30 and the vacuum tank 66 are connected, and the value of the pressure sensor 62 detecting the pressure inside the installation space 30a of the filtration port 30 is adjusted to be a predetermined value. Then, an end portion of the channel 57 on the side of the filtration port 30 is sealed. The installation space 30a of the filtration port 30 thereby becomes a sealed system, and extraction of a sample is performed by the inside of the installation space 30a being maintained in the reduced pressure state.

Referring back to FIG. 2, the preprocessing device 1 is provided with a sample transfer section 42 for transferring a sample extracted into the collection container 54 to the autosampler 101 side. The sample transfer section 42 includes a moving section 44 which moves in one direction (an arrow direction in FIG. 2) on the horizontal plane, and a transfer port 43 for installing the collection container 54 is provided on an upper surface of the moving section 44. The moving section 44 moves by operation of a drive mechanism including a rack and pinion mechanism, for example.

While a sample is not transferred to the autosampler 101 side, the transfer port 43 is arranged on the track of the holding section 25 of the transport arm 24 (the position shown by a solid line in FIG. 2). Installation of the collection container 54 in the transfer port 43 by the transport arm 24, and collection of the collection container 54 from the transfer port 43 are performed in this state.

At the time of transfer of a sample to the autosampler 101 side, the collection container 54 containing the extracted sample is installed in the transfer port 43, and then, the moving section 44 moves in an outward direction of the preprocessing device 1, and the transfer port 43 is arranged at a position adjacent to the autosampler 101 (the position shown by a broken line in FIG. 2). The sample inside the collection container 54 is sucked in, in this state, by a nozzle for sampling provided to the autosampler 101.

When suction of the sample by the autosampler 101 is ended, the moving section 44 is returned to the original position (the position shown by the solid line in FIG. 2), and the collection container 54 is collected by the transport arm 24. The used collection container 54 is transported to the discard port 34 by the transport arm 24, and is discarded. The discard port 34 is arranged near the dispensing port 32, on the track of the holding section 25 of the transport arm 24, and used separation containers 50 and collection containers 54 are discarded.

The washing port 45 for washing the sampling nozzle 20a is provided on the track of the sampling nozzle 20a. Additionally, although not shown, a washing port for washing the reagent addition nozzle 26a is provided on the track of the reagent addition nozzle 26a.

Figure 8:
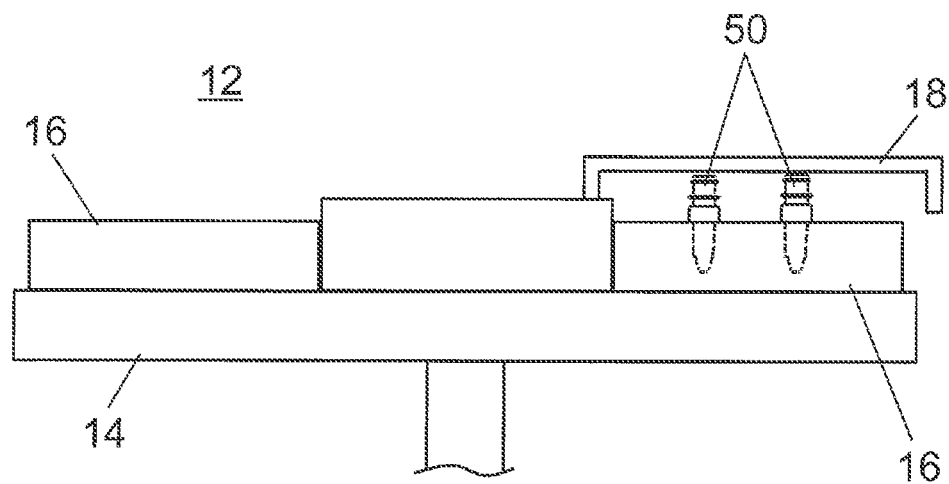
FIG. 8 is a side view showing an example structure of a container holding section.

FIG. 8 is a side view showing an example structure of the container holding section 12. As shown in FIGS. 1 and 8, in the present embodiment, a detection arm 18 is provided to the container holding section 12. The detection arm 18 extends in the horizontal direction from the center portion side of the container holding section 12 to the outer side in the radial direction. The detection arm 18 is arranged at a position slightly higher (by about 0.3 mm to 0.5 mm, for example) than the upper surface of the separation container 50 when the preprocessing kit is normally installed in the container holding section 12.

Accordingly, if all the preprocessing kits which are held by the container holding section 12 are normally installed at predetermined positions as shown in FIG. 8, the preprocessing kits will not come into contact with the detection arm 18 when the rotating section 14 of the container holding section 12 is rotated. On the other hand, if a preprocessing kit held by the container holding section 12 is not normally installed, and at least one separation container 50 is protruded above the predetermined position, this separation container 50 will come into contact with the detection arm 18 when the rotating section 14 of the container holding section 12 is rotated.

Figure 9:
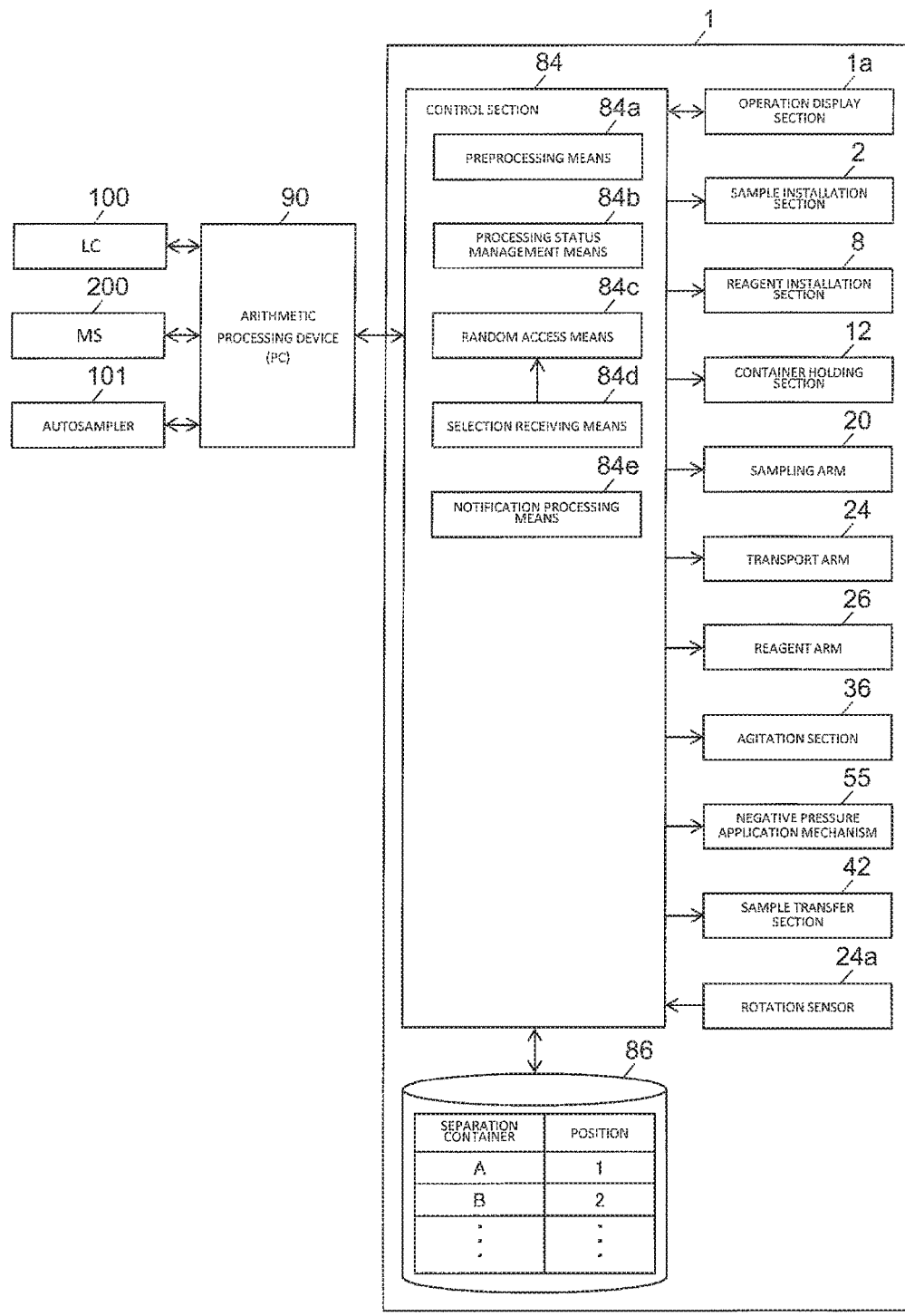
FIG. 9 is a block diagram showing an example of an electrical configuration of an analysis system.

FIG. 9 is a block diagram showing an example of an electrical configuration of the analysis system. In the following description, a "port" means one of a plurality of types of ports where the separation container 50 or the collection container 54 is to be installed, such as the filtration port 30, the dispensing port 32, the agitation port 36a, the temperature adjustment port 38, 40, or the transfer port 43.

Operation of the operation display section 1a, the sample installation section 2, the reagent installation section 8, the container holding section 12, the sampling arm 20, the transport arm 24, the reagent arm 26, the agitation section 36, the sample transfer section 42, and the negative pressure application mechanism 55 provided to the preprocessing device 1 is controlled by a control section 84. The control section 84 includes a central processing unit (CPU), for example, and functions of preprocessing means 84a, processing status management means 84b, random access means 84c, selection receiving means 84d, notification processing means 84e and the like are realized by the CPU executing programs.

An arithmetic processing device 90 configured by a personal computer (PC) or a dedicated computer, for example, is connected to the control section 84, and an analyst may manage the preprocessing device 1 by the arithmetic processing device 90. The LC 100 and the MS 200 for performing analysis of a sample which has been subjected to preprocessing by the preprocessing device 1, the autosampler 101 for injecting a sample into the LC 100, and the like are connected to the arithmetic processing device 90, in addition to the preprocessing device 1, and these devices may be automatically controlled in coordination with one another by the arithmetic processing device 90.

As described above, a plurality of sample containers is installed in the sample installation section 2, and samples contained in these sample containers are sequentially dispensed into the separation containers 50, and the separation containers 50 are transported to ports corresponding to the preprocessing items to be performed on the samples. The preprocessing means 84a performs a predetermined process corresponding to the port when the separation container 50 or the collection container 54 is installed in each port.

The random access means 84c checks the status of preprocessing at each port, and controls the operation of the transport arm 24 so that a separation container 50 preprocessing of which at a port is completed is transported to a port where next preprocessing is to be performed. That is, the random access means 84c checks the preprocessing items to be performed next on each sample, checks the vacancy status of the port corresponding to the preprocessing item, and if there is vacancy, the separation container 50 or the collection container 54 containing the sample is transported to the port. Also, if the port corresponding to the preprocessing item to be performed next on a sample is not vacant, the random access means 84c causes the target separation container 50 or collection container 54 to be transported to the port as soon as the port becomes vacant.

The processing status management means 84b manages the vacancy status of each port and the processing status at each port. The vacancy status of each port may be managed by memorizing the port where the separation container 50 or the collection container 54 was installed. Moreover, a sensor for detecting whether the separation container 50 or the collection container 54 is installed in each port or not may be provided, and the vacancy status of each port may be managed based on a signal from the sensor.

The processing status at each port may be managed based on whether a time required for preprocessing which is being performed at a port has passed since installation of the separation container 50 or the collection container 54 in the port. The status of processing at the transfer port 43 (suction of a sample by the autosampler 101) may be managed based on whether a signal indicating that sample suction has ended is received from the autosampler 101 side or not.

Now, there are provided two filtration ports 30, three agitation ports 36a, four temperature adjustment ports 38, and four temperature adjustment ports 40, and ports which perform the same preprocessing are prioritized, and the random access means 84c is configured to use ports from one with the highest priority. For example, at the time of performing filtration of a sample, if both of the two filtration ports 30 are vacant, the collection container 54 is installed in the filtration port 30 with higher priority, and the separation container 50 is installed on the collection container 54.

In the present embodiment, a storage section 86 configured by a random access memory (RAM) or a hard disk, for example, is capable of storing, in association with each other, the type of a separation container 50 and the position of the separation container 50 held in the container holding section 12. Such correspondence may be set in advance by an analyst by operation on the operation display section 1*a*, for example.

At the time of analysis of a sample, an analyst operates the operation display section 1*a*, and selects the type of the separation container 50 corresponding to the analysis item for the sample. The selection receiving means 84*d* is a selection receiving section for receiving selection of the type of the separation container 50, and the random access means 84*c* controls the operation of the transport arm 24 such that the separation container 50 of the type received by the selection receiving means 84*d* is transported from the container holding section 12. At this time, the random access means 84*c* causes the separation container 50 of the selected type to be transported from the container holding section 12, based on the correspondence stored in the storage section 86.

In this manner, an analyst may select a separation container 50 which is suitable for an analysis item, and may cause the separation container 50 to be reliably transported from the container holding section 12. Accordingly, a wider variety of analysis items may be handled, and also, preprocessing that is most suitable for the selected analysis item may be performed.

Whether the rotating section 14 of the container holding section 12 is normally operating or not may be detected by a rotation sensor 24*a*. For example, the rotation sensor 24*a* mechanically or optically detects the rotation position of the rotating section 14 to detect abnormal operation of the rotating section 14. For example, in the case where a preprocessing kit held by the container holding section 12 is protruded above the predetermined position, as described with reference to FIG. 8, the corresponding separation container 50 comes into contact with the detection arm 18, and thus, the rotating section 14 of the container holding section 12 is not able to rotate. In such a case, the abnormal operation of the rotating section 14 may be detected based on a signal from the rotation sensor 24*a*.

As described above, the detection arm 18 and the rotation sensor 24*a* configure a detection section for detecting that a separation container 50 held by the container holding section 12 is protruded above the predetermined position. Additionally, in the case where the separation container 50 and the collection container 54 are separately held by the container holding section 12, the detection section may detect that the collection container 54, not the separation container 50, is protruded above the predetermined position.

The notification processing means 84*e* notifies an analyst of abnormal operation of the rotating section 14 of the container holding section 12 by controlling display on the operation display section 1*a* based on a signal from the rotation sensor 24*a*. That is, the notification processing means 84*e* and the operation display section 1*a* configure a notification section for issuing, when it is detected that the separation container 50 is protruded above the predetermined position, a notification to the effect. Additionally, the notification section does not necessarily have to perform notification by display, and may perform notification in other modes, such as by audio, for example. Additionally, in the case where the separation container 50 and the collection container 54 are separately held by the container holding section 12, the notification section may notify to the effect that the collection container 54 is protruded above the predetermined position.

As described above, in the present embodiment, in a case where a preprocessing kit which is held by the container holding section 12 is protruded above the predetermined position due to installation error or the like, such a situation may be detected. Accordingly, an abnormality may be effectively prevented from occurring at the time of transporting the separation container 50 and the collection container 54 by the transport arm 24, and thus, the preprocessing efficiency may be increased.

Particularly, in a case where the separation container 50 and the collection container 54 are installed as a preprocessing kit in the container holding section 12 in a state where they are piled up, as in the present embodiment, the position of the separation container 50 and the collection container 54, which are piled up, is easily shifted. Accordingly, by detecting the shift in the preprocessing kit by the detection section in such a case, an abnormality may be more effectively prevented from occurring at the time of transporting the separation container 50 and the collection container 54 by the transport arm 24.

Also, in the present embodiment, an analyst is notified of an abnormality as described above, and thus, an analyst who noticed the notification may check the state of the separation container 50 and the collection container 54 which are held by the container holding section 12. Accordingly, preprocessing may be performed after the shift of the separation container 50 and the collection container 54 is surely corrected.

Figure 10:
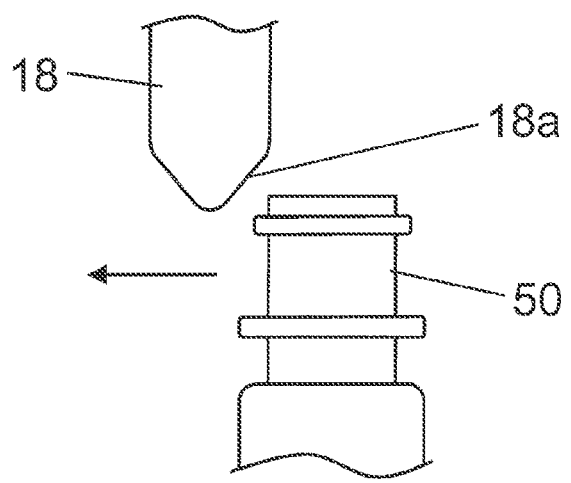
FIG. 10 is a side view showing an example modification of a detection arm.

FIG. 10 is a side view showing an example modification of the detection arm 18. In this example, as in the embodiment described above, the detection arm 18 extends in the horizontal direction from the center portion side of the container holding section 12 to the outer side in the radial direction, but this example is different from the embodiment described above in that a tapered surface 18*a* is formed to a lower portion of the detection arm 18. The lower end of the tapered surface 18*a* is arranged at a position slightly higher (by about 0.3 mm to 0.5 mm, for example) than the upper surface of the separation container 50 when the preprocessing kit is normally installed in the container holding section 12.

Accordingly, if all the preprocessing kits which are held by the container holding section 12 are normally installed at predetermined positions, the preprocessing kits will not come into contact with the detection arm 18 when the rotating section 14 of the container holding section 12 is rotated. On the other hand, if a preprocessing kit held by the container holding section 12 is not normally installed, and at least one separation container 50 is protruded above the predetermined position, this separation container 50 will come into contact with the detection arm 18 when the rotating section 14 of the container holding section 12 is rotated in the direction indicated by the arrow in FIG. 10.

Even in such a case, in the present example modification, the separation container 50 which is protruded above the predetermined position may be pushed into the container holding section 12 by the action of the tapered surface 18*a* as a pressing section. In this manner, by pushing the separation container 50 into the container holding section 12 by the tapered surface 18*a* in a case where the separation container 50 held by the container holding section 12 is protruded above the predetermined position due to an installation error or the like, preprocessing may be performed after the shift of the separation container 50 is surely corrected.

Additionally, in a case where the separation container 50 and the collection container 54 are separately held by the container holding section 12, the tapered surface 18*a* may come into contact not with the separation container 50, but with the collection container 54 which is protruded above the predetermined position. Also, the pressing section does not necessarily have to be flat-shaped like the tapered surface 18a, and it may be curved like a protruded curved surface or a recessed curved surface as long as the pressing section is capable of pushing the separation container 50 or the collection container 54 which is protruded above the predetermined position into the container holding section 12.

Figure 11A:
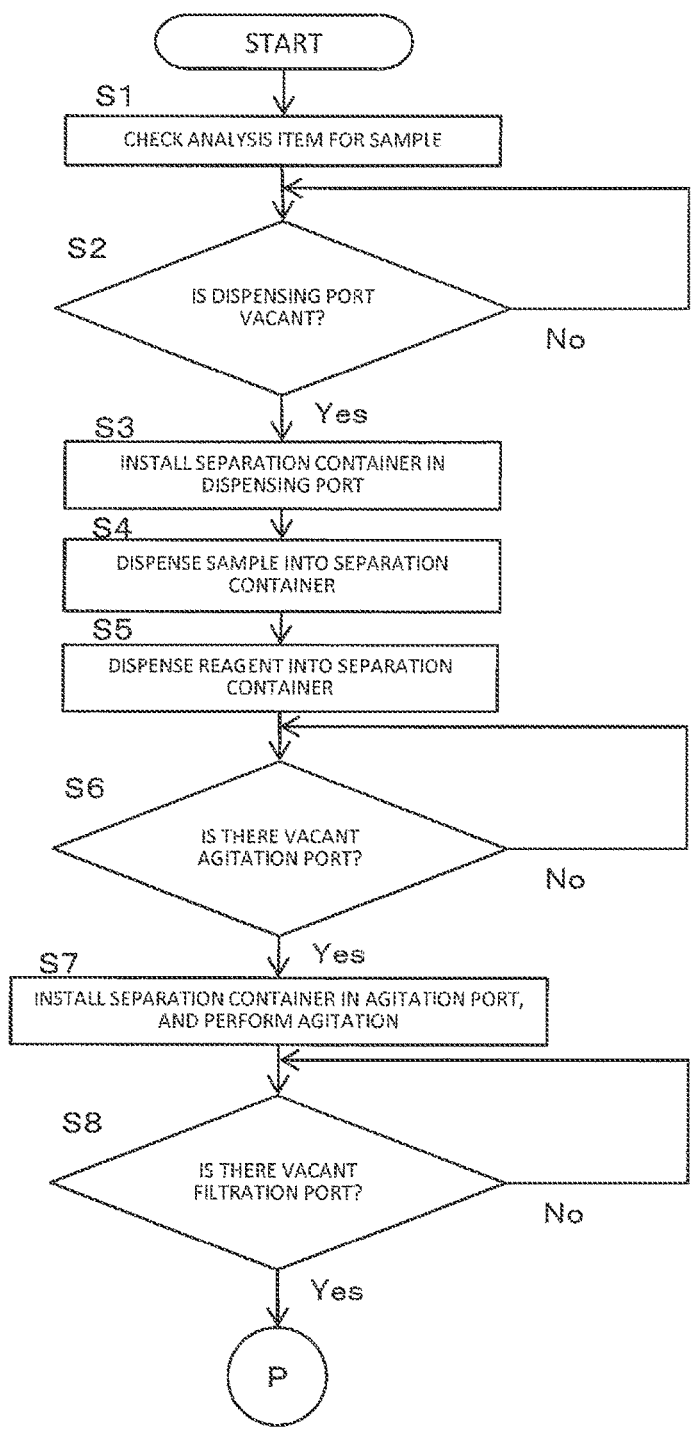
FIG. 11A is a flowchart showing example operation of the preprocessing device.
Figure 11B:
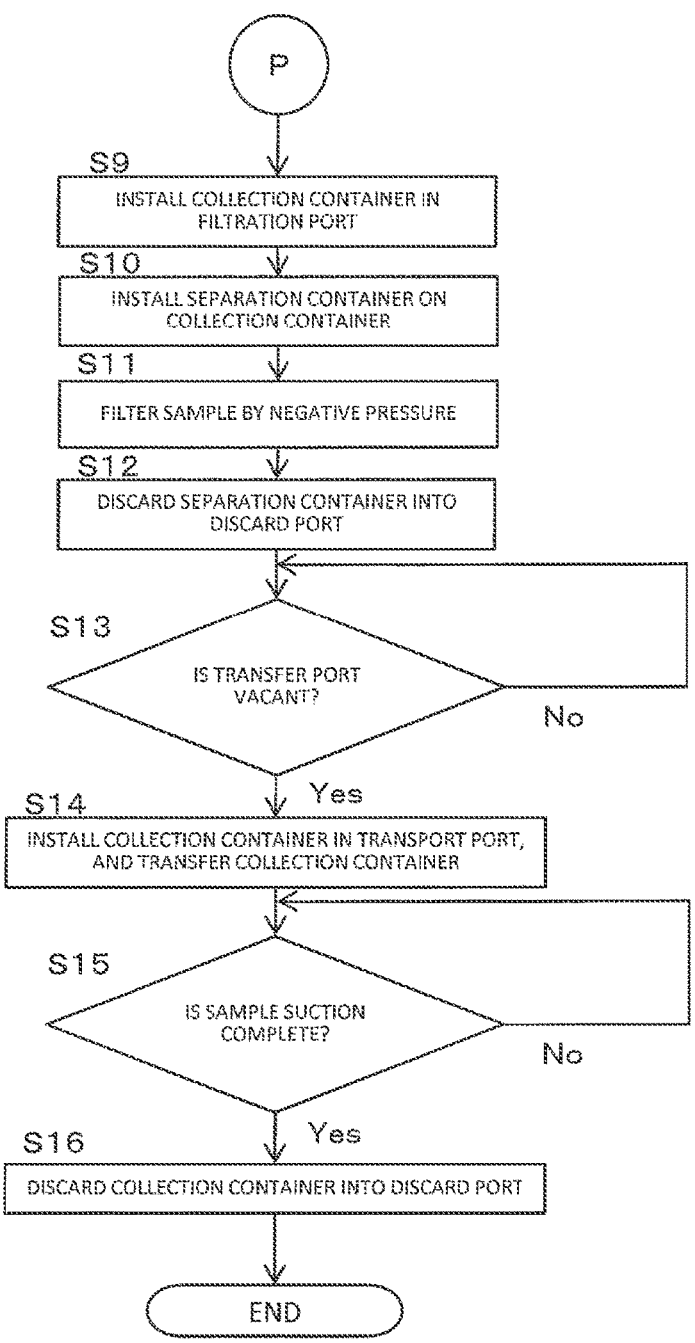
FIG. 11B is a flowchart showing the example operation of the preprocessing device.

FIGS. 11A and 11B are flowcharts showing example operation of the preprocessing device 1. In FIGS. 11A and 11B, only the flow of preprocessing for one sample is shown, but the operation for the preprocessing is performed simultaneously in parallel with and independently of the preprocessing operation for other samples. That "preprocessing is performed simultaneously in parallel and independently" means that, even while preprocessing is performed for a sample at a port, the separation container 50 or the collection container 54 containing another sample is transported by the transport arm 24 to another port, and preprocessing of the sample is independently performed.

First, an analysis item specified by an analyst, in advance, for a sample is checked (step S1), and a preprocessing item necessary to analyze the analysis item is figured out. Then, whether the dispensing port 32 is vacant is checked. If the dispensing port 32 is vacant (Yes in step S2), an unused separation container 50 for containing the sample is taken out from the container holding section 12 by the transport arm 24, and is installed in the dispensing port 32 (step S3). At this time, the separation container 50 and the collection container 54 are installed in the container holding section 12 in a state where they are piled up (the state shown in FIG. 5), but the transport arm 24 holds only the separation container 50 at the top by the holding section 25 and transports the separation container 50 to the dispensing port 32.

Then, the sample is dispensed by the sampling nozzle 20a into the separation container 50 in the dispensing port 32 (step S4). The sampling nozzle 20a which dispensed the sample into the separation container 50 is washed at the washing port 45 to be used for dispensing the next sample. A reagent according to the preprocessing to be performed on the sample is dispensed from the reagent container 10, by the reagent addition nozzle 26a, into the separation container 50 in which the sample has been dispensed (step S5). Additionally, the reagent may be dispensed into the separation container 50 before dispensing of the sample. Alternatively, a reagent dispensing port for dispensing a reagent may be provided at a position different from the dispensing port 32, and the separation container 50 may be transported by the transport arm 24 to the reagent dispensing port so that a reagent is dispensed at the reagent dispensing port.

After the sample and the reagent have been dispensed into the separation container 50 in the above manner, the vacancy status of the agitation ports 36a is checked (step S6). Then, if there is a vacant agitation port 36a (Yes in step S6), the separation container 50 in the dispensing port 32 is transported to the vacant agitation port 36a by the transport arm 24, and an agitation process is performed (step S7). This agitation process is performed for a specific time set in advance, and the sample and the reagent inside the separation container 50 are thereby mixed.

The vacancy status of the filtration ports 30 is checked during the agitation process (step S8). Then, if there is a vacant filtration port 30 (Yes in step S8), the collection container 54 is transported to the filtration port 30 by the transport arm 24 (step S9). The collection container 54 installed in the filtration port 30 at this time is the collection container 54 which is paired up with the separation container 50 where the sample is being agitated at the agitation port 36a, and is the collection container 54 which was installed in the container holding section 12 together with the separation container 50. Additionally, a different separation container 50 or collection container 54 may be transported by the transport arm 24 during this agitation process.

When the agitation process at the agitation section 36 is completed, the separation container 50 is transported by the transport arm 24 from the agitation port 36a to the filtration port 30, and the separation container 50 is installed on the collection container 54 inside the filtration port 30 as shown in FIG. 6D (step S10). At this time, the separation container 50 is pushed to the installation space 30a side by the transport arm 24 until the lower end of the skirt section 51 of the separation container 50 becomes slightly lower (by about 0.1 mm, for example) than the upper surface of the sealing member 60 provided around the filtration port 30. The sealing member 60 is thus flattened by the lower end of the skirt section 51, and the airtightness between the lower end of the skirt section 51 and the sealing member 60 is increased.

Predetermined negative pressure is applied by the negative pressure application mechanism 55 to the installation space 30a of the filtration port 30 where the separation container 50 and the collection container 54 are installed. When a state where negative pressure is applied to the installation space 30a of the filtration port 30 is maintained for a specific period of time, the sample in the separation container 50 is filtered, and the sample is extracted into the collection container 54 (step S11). A different separation container 50 or collection container 54 may be transported by the transport arm 24 also during this filtration process.

Additionally, although not incorporated in this preprocessing operation, a temperature adjustment process for maintaining the sample in the separation container 50 at a specific temperature for a specific period of time is sometimes incorporated after the agitation process for the sample in the separation container 50. In this case, the vacancy status of the temperature adjustment ports 38 is checked after the agitation process is completed, and if there is a vacancy, the separation container 50 is transported to the vacant temperature adjustment port 38. Then, the separation container 50 in the temperature adjustment port 38 is transported to the filtration port 30 after a lapse of the specific period of time, and is installed on the collection container 54 in the filtration port 30.

When the filtration process of the sample is completed, the three-way valve 64 (see FIG. 7) is switched, and the inside of the installation space 30a of the filtration port 30 is caused to reach the atmospheric pressure. Then, the used separation container 50 is taken out of the filtration port 30 by the holding section 25 of the transport arm 24, and is discarded into the discard port 34 (step S12).

Then, the vacancy status of the transfer port 43 is checked, and if the transfer port 43 is vacant (Yes in step S13), the collection container 54 in the filtration port 30 is transported by the transport arm 24 to the sample transfer section 42, and is placed on the transfer port 43. Then, the moving section 44 moves to the position on the side of the adjacent autosampler 101 (the position shown by the broken line in FIG. 2), and the collection container 54 is thereby transferred to the autosampler 101 side (step S14). On the autosampler 101 side, sample suction by the sampling nozzle is performed with respect to the collection container 54 transferred from the sample transfer section 42.

The moving section 44 is stopped at the position on the side of the autosampler 101 until sample suction by the autosampler 101 is completed, and when a signal indicating completion of sample suction is received from the autosampler 101 (Yes in step S15), the moving section 44 is returned to the original position (the position indicated by the solid line in FIG. 2). When transfer of the sample is completed, the used collection container 54 is collected by the transport arm 24 from the transfer port 43, and is discarded into the discard port 34 (step S16).

Additionally, although not incorporated in this preprocessing operation, a temperature adjustment process for maintaining the sample extracted into the collection container 54 at a specific temperature for a specific period of time is sometimes incorporated after the filtration process for the sample. In this case, the vacancy status of the temperature adjustment ports 40 is checked, and if there is a vacancy, the collection container 54 is transported to the vacant temperature adjustment port 40. Then, the collection container 54 in the temperature adjustment port 40 is transported to the transfer port 43 after a lapse of the specific period of time, and transfer of the sample is performed.

In the embodiment described above, a structure where the preprocessing kits are held in two rows by the container rack 16 is described. However, the container rack 16 may hold the preprocessing kits in one row, or in three or more rows.

Figure 12:
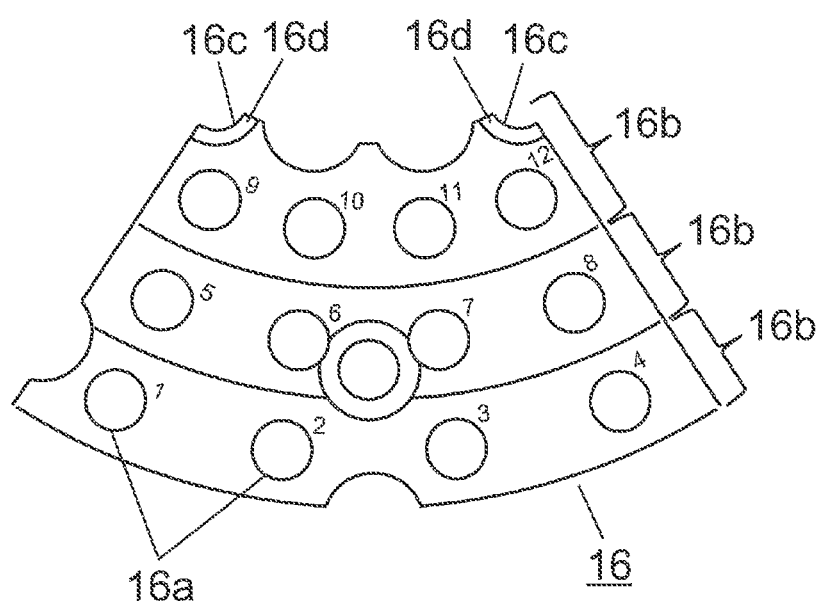
FIG. 12 is a plan view showing an example modification of a container rack.

FIG. 12 is a plan view showing an example modification of the container rack 16. In this example, the preprocessing kits are held by the container rack 16 in three rows. That is, a plurality of holding holes 16*a* is provided so as to be lined up in three rows in the radial direction in a state where the container racks 16 are arranged in a circle or an arch as shown in FIG. 2, and the preprocessing kit is held in each holding hole 16*a*.

Rows 16*b* on the upper surface of the container rack 16 where the holding holes 16*a* are formed are colored in different colors. An analyst may thereby be prevented from installing a preprocessing kit in a holding hole 16*a* in a wrong row 16*b*. Furthermore, identification information (for example, a number) used at the time of storing, in the storage section 86, the type of a separation container 50 and the position of the separation container 50 held by the container holding section 12 in association with each other is displayed on the upper surface of the container rack 16 in association with each holding hole 16*a*.

An engaging groove 16*c* is formed to each of both end portions in the circumferential direction, on the inner circumferential side, of the upper surface of the container rack 16. At the time of installing the container rack 16 on the rotating section 14 of the container holding section 12, the container rack 16 is positioned by pins (not shown) provided to the rotating section 14 side being engaged with the engaging grooves 16*c*. The pins are colored, and circumferential edge portions 16*d* of the engaging grooves 16*c* on the upper surface of the container rack 16 are colored in the same color as the pins, for example. An analyst may thereby smoothly install the container rack 16 on the rotating section 14.

The embodiment described above has a configuration according to which a sample in the separation container 50 is separated by reducing the pressure inside the installation space 30*a* of the filtration port 30 to a negative pressure level. However, such a configuration is not restrictive, and a sample in the separation container 50 may alternatively be separated by increasing the pressure inside the separation container 50.

The control section 84 of the preprocessing device 1 and the arithmetic processing device 90 do not necessarily have to be provided separately, and operation of the entire analysis system may alternatively be controlled by one control section. Also, a sample which has been subjected to preprocessing by the preprocessing device 1 does not necessarily have to be introduced into the LC 100 or the MS 200, and may alternatively be introduced into another device.

DESCRIPTION OF REFERENCE SIGNS

1 preprocessing device
1*a* operation display section
2 sample installation section
4 sample rack
6 sample container
8 reagent installation section
10 reagent container
12 container installation section
14 rotating section
16 container rack
16*a* holding hole
16*b* row
16*c* engaging groove
16*d* circumferential edge portion
18 detection arm
18*a* tapered surface
20 sampling arm
20*a* sampling nozzle
20 vertical shaft
22 transport arm
24*a* rotation sensor
25 holding section
26 reagent arm
26*a* reagent addition nozzle
29 vertical shaft
30 filtration port
30*a* installation space
31 holding member
32 dispensing port
34 discard port
36 agitation section
36*a* agitation port
38 temperature adjustment port
40 temperature adjustment port
42 sample transfer section
43 transfer port
44 moving section
45 washing port
50 separation container
50*a* inner space
50*b* opening
50*c* flange section
50*d* extraction opening
51 skirt section
52 separating layer
54 collection container
54*a* inner space
54*b* opening
54*c* flange section
54*d* cut-out
55 negative pressure application mechanism
56 channel
57 channel
58 vacuum pump
60 sealing member
62 pressure sensor
64 three-way valve
66 vacuum tank
68 pressure sensor 70 three-way valve
84 control section
84a preprocessing means
84b processing status management means
84c random access means
84d selection receiving means
84e notification processing means
86 storage section
90 arithmetic processing device
100 liquid chromatograph (LC)
101 autosampler
200 mass spectrometry device (MS)
201 ionization section
202 mass spectrometry section

The invention claimed is:

1. A preprocessing device comprising:
a container holding section configured to hold a plurality of containers including a separation container with a separating layer through which a specific component in a sample is separated and a collection container for collecting a sample extracted by the separating layer;
a filtration section configured to separate a sample by the separating layer by applying pressure to a sample in the separation container; and
a transport section configured to transport a container held by the container holding section from a predetermined transport position,
wherein the filtration section is separate from the container holding section; and
wherein the container holding section is configured to hold the plurality of containers in an annular or arch-shaped holding region formed outside a circumference of the filtration section, and is configured to sequentially move the plurality of containers to the transport position by shifting the plurality of containers in a circumferential direction of the holding region.

2. The preprocessing device according to claim 1, further comprising the separation container and the collection container, wherein the separation container and the collection container are installed in the container holding section in a state where the separation container and the collection container are piled up.

3. The preprocessing device according to claim 1, wherein the container holding section includes a rotating section that rotates on a horizontal plane, and a plurality of container racks that can be detachably mounted to the rotating section, each container rack being for holding a plurality of containers.

4. The preprocessing device according to claim 1, further comprising a detection section configured to detect that a container held by the container holding section is protruded above a predetermined position.

5. The preprocessing device according to claim 4, further comprising a notification section configured to issue a notification about protrusion in a case where protrusion of a container above the predetermined position is detected by the detection section.

6. The preprocessing device according to claim 1, further comprising a pressing section configured to push a container held by the container holding section into the container holding section in a case where the container is protruded above a predetermined position.

7. The preprocessing device according to claim 1, further comprising a plurality of types of separation containers held by the container holding section,
the preprocessing device further includes
a storage section configured to store, in association with each other, a type of the separation container and a position of the separation container held by the container holding section, and
a selection receiving section configured to receive selection of a type of the separation container, and
the transport section is configured to transport the separation container of a selected type from the container holding section according to correspondence stored in the storage section.

8. An analysis system comprising:
the preprocessing device according to claim 1;
a liquid chromatograph into which a sample extracted by the preprocessing device is to be introduced; and
a control section configured to automatically control the preprocessing device and the liquid chromatograph in coordination with each other.

9. An analysis system comprising:
the preprocessing device according to claim 1;
a mass spectrometry device into which a sample extracted by the preprocessing device is to be introduced; and
a control section configured to automatically control the preprocessing device and the mass spectrometry device in coordination with each other.

10. The preprocessing device according to claim 1, wherein all parts of the filtration section are located closer to a center axis of the annular or arch-shaped holding region than all parts of the annular or arch-shaped holding region.

11. The preprocessing device according to claim 1, the transport section further comprising a holding section configured to move along an arch-shaped track, the arch-shaped track passing the filtration section and the transport position.

* * * * *